United States Patent [19]
Adami et al.

[11] Patent Number: 5,714,458
[45] Date of Patent: Feb. 3, 1998

[54] STABLE PHARMACEUTICAL COMPOSITIONS CONTAINING A FIBROBLAST GROWTH FACTOR

[75] Inventors: Marco Adami; Rosanna Dalla Casa, both of Milan, Italy; Luciano Gambini, Cornaredo; Roberto Magrini, Bresso; Rosaria Mariani, Desio; Giovanni Perrone, Milan, all of Italy

[73] Assignee: Farmitalia Carlo ERBA S.r.l., Milan, Italy

[21] Appl. No.: 325,632

[22] Filed: Oct. 19, 1994

Related U.S. Application Data

[63] Continuation of Ser. No. 966,077, Jan. 19, 1993, abandoned.

[30] Foreign Application Priority Data

Jul. 18, 1990 [GB] United Kingdom ............... 9015824

[51] Int. Cl.$^6$ ............... A61K 38/18; C07K 14/50
[52] U.S. Cl. ............... 514/2; 435/69.1; 435/69.4; 530/350; 530/399
[58] Field of Search ............... 435/69.1, 69.4; 514/2, 12; 530/350, 399

[56] References Cited

U.S. PATENT DOCUMENTS 5,037,644  8/1991  Shaked et al. ............... 424/85.2
5,217,954  6/1993  Foster et al. .

FOREIGN PATENT DOCUMENTS

| | | |
|---|---|---|
| 0 193 917 | 9/1986 | European Pat. Off. . |
| 0267015 | 5/1988 | European Pat. Off. . |
| 0308238 | 3/1989 | European Pat. Off. . |
| 0312208 | 4/1989 | European Pat. Off. . |
| 0345660 | 12/1989 | European Pat. Off. . |
| 0406856 | 1/1991 | European Pat. Off. . |
| WO91/09610 | 7/1991 | WIPO . |

OTHER PUBLICATIONS

Budavari et al., eds., The Merck Index, Eleventh Ed., 1989, Merck & Co., Inc., Rahway, NJ, p. 278, No. 1835.

Fox et al., The Journal of Biol. Chem., vol. 263, pp. 18452–18458, 1988.

R.R. Lobb, "Clinical Applications of Heparin–Binding Growth Factors, "European Journal of Clinical Investigations, vol. 18 (1988), pp. 321–336.

D. Gospedarowicz et al. "Heparin Protects Basic and Acidic FGF From Inactivation, "Journal of Cellular Physiology, vol. 128 (1986), pp. 475–484.

Abraham et al., 1986, Embo J. 5, 2523.

*Primary Examiner*—Stephen Walsh
*Assistant Examiner*—Sally P. Teng
*Attorney, Agent, or Firm*—Oblon, Spivak, McClelland, Maier & Neustadt, P.C.

[57] ABSTRACT

A stable lyophilized formulation of a fibroblast growth factor (FGF) comprises the FGF, a pharmaceutically acceptable bulking agent and either (a) an alkali metal salt of a carboxyalkyl cellulose, or (b) a polyoxyethylene sorbitan fatty acid ester and cysteine.

32 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 155 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:1:

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

STABLE PHARMACEUTICAL COMPOSITIONS CONTAINING A FIBROBLAST GROWTH FACTOR

This application is a continuation of application Ser. No 07/966,077, filed Jan. 19, 1993, now abandoned, which is a 371 application of international application PCT/EP91/01330, filed Jul. 16, 1991.

The present invention relates to freeze dried (lyophilized) compositions containing fibroblast growth factor (FGF) having human mitogenic activity, in particular, human basic fibroblast growth factor (bFGF). The bFGF may be natural or produced by recombinant means.

Safe handling and administration of protein drugs represent significant challenges to pharmaceutical formulators as proteins possess unique chemical and physical properties which pose difficult stability problems: a variety of degradation pathways exist of proteins, involving both chemical and physical instability. These macromolecules are also at risk from microbial degradation due to adventitious contamination of the solutions during purification or storage. All these considerations are especially critical for the pharmaceutical manufacturer who is formulating and packaging these agents with the expectation of an economically favorable shelf-life. Thus, a thorough preformulation programme is an essential step for protein drugs, to solve their possible formulation problems. In addition, a range of stability-indicating test methods is necessary, in order to ensure shelf-life is maintained.

Many biological materials, including proteins which will rapidly deteriorate even in frozen solutions, can be kept in a viable state for long periods of time by lyophilization of the material. Lyophilization (also known as freeze drying) is a process of drying a composition in which water is sublimed from the composition after it is frozen. The particular advantages of this process are that materials which are relatively unstable in an aqueous solution can be processed and filled into dosage containers in the liquid state, taking advantage of the relative ease of processing of a liquid; dried without elevated temperatures, thereby eliminating adverse thermal effects; and then stored in the dry state in which there are relatively few stability problems. Thus, the product can be stabilized against loss of biological activity to provide a long shelf life.

It is often impractical to design formulations based merely on the lyophilization of the bulk drug. This is so because usually the amounts of the drug used in the formulation will be very small. This is a problem because during the lyophilization process the drug can be pulled from the lyophilization container by the vacuum employed in the process. Furthermore, many polypeptides are relatively unstable when lyophilized in small concentrations. They can absorb to product packaging and lose activity. Many lyophilized pharmaceutical compositions rely on the use of diluent or extender to increase the amount of solid present during the lyophilization process and thereby eliminate the problems associated with lyophilization of small amounts of bulk drug.

EP-A-0 308 238 describes stable lyophilized compositions comprising a polypeptide growth factor having human mitogenic activity and a water soluble or water swellable, pharmaceutically acceptable polymer capable of imparting viscosity to a reconstituted solution of the composition. As a growth factor, epidermal growth factor (EGF) is particularly mentioned.

The present invention provides a lyophilized composition which comprises a fibroblast growth factor (FGF), a pharmaceutically acceptable bulking agent and either:

(a) an alkali metal salt of a carboxyalkyl cellulose, or
(b) a polyoxyethylene sorbitan fatty acid ester and cysteine.

In this application, FGF includes the class of polypeptides that have biological activity similar to that exhibited by the natural human FGF polypeptide. Thus, FGF includes acidic and basic FGF, such as human FGF produced by recombinant DNA techniques or derived from natural sources, as well as closely related mammalian FGF, eg. bovine, murine or rodent. FGF also includes chemically modified FGF such as a FGF in which at least one of the four cysteine aminoacid residues are derivatized. A FGF for use in the invention may therefore be a carboxymethylated FGF wherein the —SH group of one or more of cysteine residues has been converted into a —S—CH$_2$—COOH group. Any bFGF molecule as described in, for instance, WO 86/07595; WO 87/01728; EP-A-0226181; Abraham et al, EMBO J. 5, 2523–2528, 1986; or Lobb, Eur. J. Clin. Invest. 18, 321–336, 1988; may be usefully employed in the invention.

A mixture of bFGFs may be employed. This may be an approximately 50:50 mixture of:

a 154 amino acid human bFGF having the amino acid sequence of the 155 amino acid form which is reported by Abraham et al and shown in SEQ ID NO:1 but without the N-terminal Met residue; and a 153 amino acid human bFGF having the amino acid sequence shown in SEQ ID NO:1 but without the N-terminal Met and Ala residues.

Human basic FGF, for example produced by recombinant DNA techniques, is preferred for use in the present invention. A specific carboxymethylated FGF for use in the invention is the 146 amino acid form of bFGF, as described in WO 87/01728, wherein the two cysteine residues at positions 69 and 87 are irreversibly blocked by carboxymethyl groups, i.e. as —S—CH$_2$—COOH groups. This specific carboxymethylated FGF will be referred to as CM-FGF. It is therefore a bFGF having the amino acid sequence from position 10 to position 155 shown in SEQ ID NO:1 in which the Cys residues at positions 78 and 96 in SEQ ID NO:1 are carboxymethylated.

In one embodiment of the present invention the composition further includes an antioxidant, selected to prevent substantially oxidation of the FGF when the composition of the invention is stored over an extended period of time, eg. 1–3 months. Preferably the anti-oxidant is dithiothreitol (DTT). When present, the antioxidant will typically be present in an amount of from 0.01% to 100%, preferably from 0.1% to 25% by weight of the bulking agent.

The bulking agent is any bulking agent suitable for use in freeze-drying. The bulking agent generally has good properties as a rigidizer, in order to avoid melt-back or collapse of the product during lyophilization. Suitable pharmaceutically acceptable bulking agents include mannitol, lactose, polyvinylpyrrolidone, galactitol and trehalose. Of these, mannitol is preferred. The amount of FGF in the composition of the present invention is typically from 0.01% to 5%, preferably 0.1 to 1%, of the weight of the bulking agent.

It has surprisingly been found that the FGF in admixture with a pharmaceutically acceptable bulking agent may be stabilized by the presence of an alkali metal salt of a carboxyalkyl cellulose, for example a carboxy $C_{1-4}$ alkyl cellulose. The alkali metal salt may be for example the sodium salt or potassium salt. This component will usually be present in an amount from 0.1% to 50%, preferably from 2.5% to 10%, by weight of the bulking agent. Sodium carboxymethyl cellulose is preferred. The use of a cellulose salt surprisingly provides stability to compositions of the present invention which is not obtainable from neutral alkyl cellulose, eg. methyl cellulose.

Compositions of the present invention may also be stabilized by the use of a polyoxyethylene sorbitan fatty acid ester and cysteine. It has surprisingly been found that these two components act synergistically to provide increased stability. Examples of polyoxyethylene sorbitan fatty acid esters include partial $C_{12-20}$ saturated or unsaturated fatty acid esters of sorbitol and its mono- and di-anhydrides copolymerised with ethylene oxide. Typically, from 10 to 40, for example about 20 moles of ethylene oxide for each mole of sorbitol and its anhydrides will be present. Polyoxyethyle sorbitan fatty acid esters are known generally as polysorbates. Examples of polysorbates include polysorbate 20 (polyoxyethylene 20 Sorbitan Monolaurate, Chemical Abstracts reference No 9005-64-5), which is a mixture of partial lauric esters of sorbitol and its mono- and di-anhydrides copolymerised with approximately 20 moles of ethylene oxide for each mole of sorbitol and its anhydrides, polysorbate 40 (polyoxyethylene 20 sorbitan monopalmitate, CAS No 9005-66-7), polysorbate 60 (polyoxyethylene 20 sorbitan mono-stearate CAS No 9005-67-8), polysorbate 65 (polyoxyethylene 20 sorbitan tristearate, CAS No. 9005-71-4, polysorbate 80 (polyoxyethylene 20 sorbitan mono-oleate, CAS No 9005-65-6) and polysorbate 85 (polyoxyethylene 20 sorbitan trioleate CAS No 9005-70-3). The amount of the polyoxyethylene sorbitan fatty acid ester is preferably from 0.01% to 25%, most preferably from 0.1% to 1% by weight of the bulking agent. The amount of cysteine in compositions of the invention is preferably from 0.001% to 1%, most preferably 0.01% to 0.1% by weight of the bulking agent.

Compositions of the present invention will normally be formulated in bulk solution prior to freeze drying. The bulk solution may be freeze-dried in any quantity, although preferably the bulk solution will be divided into aliquots containing from 5 to 500, for example from 10 to 100 and preferably 50 micrograms of FGF. These aliquots will be freeze-dried separately, eg. in individual glass vials. Before the solution is freeze-dried, it may be sterilized for example by filtration. A 0.2 μm nylon membrane filter may be used for this purpose. Using HPLC analysis carried out after such filtration, we have found that FGF is consistently recovered on a quantitative basis.

Lyophilization essentially consists of the following steps. First, the solution to be freeze-dried is frozen at a temperature below its eutectic temperature in an evacuation chamber. The chamber is then evacuated, usually below 13.3 Pa (0.1 Torr). Ice is sublimed on a cold condensing surface at a temperature below that of the product, the condensing surface being within the chamber or in a connecting chamber. Then, heat is introduced to the product under controlled conditions, thereby providing energy for sublimation at a rate designed to keep the product below its eutetic temperature. A typical freeze-drying cycle is as follows:

(a) Freeze at −45° C., and maintain this temperature for four hours.

(b) Primary drying at −45° C. to +25° C. for approximately twelve hours, with vacuum level less than 13.3 Pa (0.1 Torr) and a condenser temperature of −60° C.

(c) Secondary drying at +25° C. for approximately eleven hours, with the same vacuum and condenser temperature as described in (b) above. We have found this freeze-drying cycle to be suited to preparation of batches of FGF produced in accordance with the present invention. However, it will be apparent to those of ordinary skill in the art that variations of this protocol which do not substantially alter the stability of the FGF may be made.

Aliquots of the composition of the present invention may be dispensed into sterile vials. Sterile glass vials can be suitable. It is known that proteins adhere to glass surfaces, and we have found that when the lyophilized compositions of the present inventions is reconstituted in a glass vial, some loss of protein due to adhesion occurs. However, we have found that coating the glass vials with silicone emulsion (Pharmaceutical grade) in order to minimise sticking successfully overcomes this problem.

We have also observed that when the glass vials are sealed with conventional rubber stoppers, losses of protein may occur due to absorption of the FGF to the rubber surfaces. The use of fluororesin laminated butyl rubber stoppers prevents this absorption process.

The lyophilized compositions of the present invention may be stored under air or vacuum. Preferably however, they will be stored under an inert gas, eg. nitrogen.

The lyophilised composition of the invention therefore consists essentially of a FGF, a pharmaceutically acceptable bulking agent and either (a) an alkali metal salt of a carboxyalkyl cellulose or (b) a polyoxyethylene sorbitan fatty acid ester and cysteine.

The freeze-dried composition of the invention may be reconstituted using any pharmaceutically acceptable solvent. Preferably, the solvent used will provide a reconstituted solution with a pH of between 5.0 and 7.0. Preferably, a 0.9% solution of sodium chloride (i.e. physiological saline) is the reconstitution solvent. Optionally, the solution contains an effective amount of an anti-microbial preservative agent. Benzalkonium chloride at a concentration of about 0.005% by weight is particularly suitable, since its efficacy is well documented and because it is commonly used in pharmaceutical formulations, for example as an opthalmic preservative. We have found that 0.005% by weight benzalkonium chloride effectively inhibits microbial activity in reconstituted solutions of the present invention.

FGF is a growth factor that plays a role in the regulation of growth of normal human cells. FGF has utility in stimulating wound healing and the growth fibroblast cells. The present invention thus also provides a kit containing the lyophilized composition described above in a sterile vial and a sterile diluent for reconstitution of the lyophilized composition. The invention further includes a method of preparing an aqueous FGF solution which comprises reconstituting the freeze dried composition of the present invention with an aqueous diluent, eg. the pharmaceutically acceptable solvent described above. The compositions or kits according to the present invention are useful in a method of treatment of the human or animal body, eg. in the treatment of wound healing.

The Examples which follow illustrate aspects of the present invention.

In the following Examples, the FGFs used are the basic FGF FCE 26184 which is a recombinant protein drug available from Farmitalia Carlo Erba Biotechnology Development Department and CM-FGF which is a chemically modified protein obtained from bFGF (146 amino acid form). Their preparation is described below in the Preparation Examples. bFGF and CM-FGF are obtainable as a frozen bulk solution at a concentration of active substance of approximately 2.0 mg/ml for bFGF and 1.1 mg/ml for CM-FGF (this concentration is expressed as protein content measured by the biruet reaction, the solvent is at pH 6.0 obtained with a 10 μM phosphate buffer).

We have observed that thawing these bulk solutions and diluting them to a concentration of about 50 μg/ml using a 2% mannitol solution does not affect protein stability. HPLC analyses of diluted solutions show active drug substance (bFGF or CM-FGF) is quantitatively recovered.

Preparation Example 1
Preparation of bFGF (FCE 261841)

The construction of the synthetic DNA sequence for bFGF and of the expression plasmid carrying such sequence was performed according to the procedure described in EP-A-363675. The fermentation and purification process was carried out as follows:

(a) Fermentation process A bacterial strain, E. coli type B, from the Institute Pasteur collection, was transformed with a plasmid carrying both the human gene coding for bFGF and the gene for tetracycline resistance. This transformed strain was used for the production of recombinant non-glycosylated h-bFGF (human bFGF). A Master Cell Bank (15 freeze-dried vials) and a Working Cell Bank (W.C.B.) (70 vials stored in liquid nitrogen at −190° C.) of this strain were prepared. The content of one vial of W.C.B. was used as the inoculum for the fermentation phase.

The fermentation process was carried out in 10 l fermentors filled with 4 l of culture medium. Tetracycline hydrochloride was added to the medium in order to maintain the conditions of strain selection. After 20 hours of growth at 37° C. the final biomass was 42±2 g/l dry weight, and the production of bFGF was 2500±500 mg/l as measured by comparative gel electrophoresis.

Enrichment in pure oxygen was required during the fermentation phase in order to allow a large bacterial growth.

(b) Initial purification The cells (microorganisms) were separated from the total fermentation broth by centrifugation. The resulting pellet was resuspended in a sodium phosphate buffer containing sodium chloride. A minimum of 3 passages through a high pressure homogenizer were necessary for efficient cell breakage. The resulting cell lysate was clarified by centrifugation and the supernatant was collected for further processing.

(c) purification The clarified supernatant was loaded on a column of Sepharose (Trade Mark) S Fast Flow (cation exchanger) and the product was eluted from this column using a gradient of increasing sodium chloride concentrations in a phosphate buffer. The product was further purified on a column of Heparin Sepharose (Trade Mark) 6 B by eluting with a gradient of increasing sodium chloride concentration in a phosphate buffer. Finally a buffer exchange was made on a Sephadex (Trade Mark) G25 resin to obtain the product in the bulk product buffer (Sodium phosphate -EDTA).

(d) Column sanitization Sepharose S Fast Flow and Sephadex G25 columns were sanitized by washing with sodium hydroxide solutions. Heparin Sepharose was washed alternatively with solutions at pH=8.5 and pH=5.5 containing 3M sodium chloride.

In this way, there was obtained bFGF designated FCE 26184. This is an approximately 50:50 mixture of:
- a 154 amino acid human bFGF having the amino acid sequence of the 155 amino acid form which is reported by Abraham et al and shown in SEQ ID NO:1 but without the N-terminal Met residue; and
- a 153 amino acid human bFGF having the amino acid sequence shown in SEQ ID NO:1 but without the N-terminal Met and Ala residues.

Preparation Example 2
Preparation of CM-FGF

To a solution of 100 mg of recombinant human bFGF (146 aminoacid form), obtained as described in WO 87/01728, in 110 ml of 25 mM phosphate buffer pH 8.0/5 mM EDTA, was added 400 mg of iodoacetic acid in 110 ml of the same buffer. The reaction mixture was allowed to stand at room temperature for two hours in the dark. The reaction mixture was then directly loaded on a MonoS column (HR 10/10, Pharmacia) equilibrated in 25 mM phosphate buffer pH 7.5. In order to eliminate the reagent excess, the column was extensively washed with the equilibration buffer and the carboxymethylated bFGF (CM-FGF) was eluted with a linear gradient from 0 to 1M NaCl in 25 mM phosphate buffer pH 7.5. The CM-FGF containing fractions were desalted on a Sephadex G-25 column (Pharmacia) equilibrated in 10 nM phosphate buffer pH 6.0/0.1 mM EDTA.

EXAMPLE 1

We have found that the presence of an antioxidant, eg. 1,4-dithiothreitol (DTT) is effective in protecting the protein in solution against oxidation.

However, in spite of its good protective effect in solution, DTT does not inhibit degradation of the protein in the freeze-dried state when it is stored over an extended period of time. In fact a 50 µg freeze-dried formulation of bFGF containing mannitol as a bulking agent and DTT as antioxidant did not yield an acceptable stability: a potency loss (HPLC method) of about 10% was detected after storage for one week at 35° C. and 25° C. Thus the need existed to incorporate a protective agent into the formulation.

According to P. P. De Luca and M. W. Townsend (Journal of Parenteral Science and Technology. vol. 42, No. 6, Nov.-Dec. 1988, page 190) "prevention and reduction of conformational modifications in proteins due to freezing, drying, or extended storage may be attained through the use of lyo- or cryo-protectans. A lyoprotectant is being defined as a compound that stabilizes and prevents the degradation of a protein both during freeze-drying and afterwards, during storage, whereas a cryoprotectant only infers protection from freezing damage".

Based on these theoretical considerations, experimental work was thus undertaken to determine the FCE 26184 and CM-FGF protective capacity of a number of compounds which might act as lyoprotectants.

Hydroxypropylmethylcellulose (HPMC), sodium carboxymethyl cellulose (NaCMC), methylcellulose (MC), hydroxyethylcellulose (HEC), polyvinyl alcohol (PVA), sodium chloride, glycine, cysteine and albumin were selected as possible protective agents. Solutions containing bFGF (50 µg/ml), mannitol (20 mg/ml as bulking agent, DTT (either 0.5 or 0.1 mg/ml) as antioxidant, and a suitable concentration of each potential stabilizer were prepared aseptically, filled into vials (nominal volume: 1.0 ml), and freeze-dried. The effect of storage on the protein potency in the final freeze-dried formulation was checked through accelerated stability studies (35° C.).

Basic experimental results are summarized in Table 1. As already mentioned, the freeze-dried formulation containing mannitol and DTT underwent 10% potency loss after one week storage.

A loss of the same extent was observed when cysteine was added with the aim of exploiting its synergism with DTT.

The presences of a lyoprotectant, such as NaCMC significantly improved protein stability. Other cellulose derivatives (HPMC, HEC, MC) proved to be ineffective as stabilizers (data are presented in Table 1 only for MC, but other derivatives behaved similarly).

PVA, sodium chloride, glycine and albumin proved to be highly incompatible with bFGF. Polysorbate 80 or cysteine proved to be ineffective, if used alone. However the combination of polysorbate 80 and cysteine surprisingly worked well as a stabilizer. Furthermore, either polysorbate 80 or cysteine acted synergistically with NaCMC.

Data presented in Table 1 put into evidence the key role played by the lyoprotectants as stabilizing agents for the protein in the freeze-dried state. Possible mechanism for the protective capacity of these compounds could reside in their ability to prevent the segregation of water from the protein in the freeze-dried preparation. In each freeze-dried formulation tested, water is present (as residual humidity) to an extent exceeding that of the drug and sufficient to maintain the protein in a hydrated conformation. Any challenge (temperature: low, or high; solvents) which disrupts the shell of water loosely coordinated by the protein structure brings about a protein inactivation through denaturation or aggregation. Stabilizers such as NaCMC are able to tightly coordinate water molecules through either their hydrophilic structure of their polar carboxylic group. As consequence, they maintain the protein microenvironment in a hydrated state.

Other cellulose derivatives, such as HPMC, MC, and HEC, tested as protecting agents, provided to be ineffective, most probably because they lack carboxylic group.

The low stabilizing activity of polysorbate 80 might be expected, due to the low coordination power of this additive towards the water molecules. On the contrary, the synergistic effect of polysorbate 80 with both cysteine and NaCMC was quite unexpected.

TABLE 1

PCE 26184 preformulation studies
Accelerated stability results of different
freeze-dried formulations, containing bFGF (50
mcg), Mannitol (20 mg), and DTT (0.1 mg)

| COMPOSITION | | | | Residual PCE 26184 % (HPLC assay) after 1 week at | | |
|---|---|---|---|---|---|---|
| MC | NaCMC | Cysteine | Polysorbate 80 | 4° C | 25° C | 35° C |
| — | — | — | — | 91.0 | 88.0 | 89.0 |
| 1 | — | — | — | 59.3 | — | 32.0 |
| — | — | 0.02 | — | 93.0 | 83.0 | 70.0 |
| — | 1 | — | — | 99.0 | 102.0 | 102.0 |
| — | — | — | 0.1 | 92.0 | 88.0 | 88.0 |
| — | — | 0.01 | 0.01 | 106.0 | 105.0 | 112.0 |
| — | 0.01 | — | 0.05 | 96.0 | 100.0 | 97.0 |
| — | 0.01 | 0.01 | — | 108.0 | 114.0 | 113.0 |

Experimental results for CM-FGF are summarized in Table 2, in which n.d. means not determined. Solutions containing CM-FGF (50 µg/ml), mannitol (20 mg/ml) as bulking agent, DTT (0.1 mg), and a suitable concentration of each potential stabilizer were prepared aseptically, filled into vials (nominal volume 1.0 ml), and freeze dried. The effect of storage on the protein potency in the final freeze dried formulation was checked through accelerated stability studies (35° C./45° C.). As already seen for bFGF, Na-CMC significantly improves CM-FGF stability.

TABLE 2

CM-FGF preformulation studies. Accelerated stability results of different freeze dries formulations, containing CM-FGF (50 µg) and mannitol (20 mg)

| COMPOSITION (mg/vial) | | | | RESIDUAL CM-FGF (HPLC ASSAY) | | | | | |
|---|---|---|---|---|---|---|---|---|---|
| NaCMC | CYSTEINE | Polysorbate 80 | DTT | T=0 | 15 DAYS | | DAYS | | |
| | | | | | 35°C. | 45°C. | 4° C. | 25° C. | 35° C. |
| — | — | — | — | (%) 100.00 | n.d. | n.d. | 99.86 | 83.36 | 74.30 |
| — | — | — | 0.10 | (%) 100.00 | 91.13 | 84.11 | 82.29 | 76.82 | 72.77 |
| 1.00 | — | — | — | (%) 100.00 | 87.58 | 86.50 | n.d. | 96.58 | 81.30 |
| 1.00 | — | — | 0.10 | (%) 100.00 | n.d. | 98.25 | 104.99 | 101.31 | 105.79 |

HPLC assay of the samples was performed using the following materials, equipment and solutions, under the conditions provided below.

Materials bFGF frozen bulk solution, working standard CM-FGF frozen bulk solution, working standard Acetonitrile, HPLC grade Water, HPLC grade Trifluoroacetic acid, analytical grade 1,4-dithiothreitol, analytical grade Equipment Liquid chromatograph Milton Roy model CM 4000, or equivalent, equipped with:

chromatographic column: (length 250 mm, internal diameter 4.6 mm) filled with Vydac 218TP54 300 A (average particle size 5 mcm), or equivalent injection valve: Rheodyne model 7125, or equivalent, fitted with a 100 mcl sample loop detector Shimadzu model SFD 6A, or equivalent integrating recorder: SP 4270 (Spectra-Physics), or equivalent Membrane filter, 0.22 µm porosity, Millipore Durapore GVWP, or equivalent High precision laboratory glassware Plastic pipet tips (Gilson)

Automatic pipets (Gilson)

Disposable plastic microtubes, capacity 2.5 ml (Eppendorf)

Solutions

Mobile phase (A) consisting of water, containing 0.1% of trifluoracetic acid (w/v), filtered through the membrane filter and deaerated.

Mobile phase (B) consisting of 95% acetonitrile-5% water containing 0.1% of trifluoroacetic acid (w/v), filtered through the membrane filter and deaerated.

1,4-dithiothreitol solution Prepare a solution containing about 1 mg/ml in HPLC grade water Standard solution Transfer a suitable volume of bulk solution of bFGF or CM-FGF working standard, accurately measured, into a disposable plastic microtube. Dilute with a suitable volume of 1,4-dithiothreitol solution in order to obtain a final solution containing about 50 mcg/ml of bFGF or CM-FGF. The standard solution must be freshly prepared and used within a working day.

Sample solution Prepare the sample solution using at least five freeze-dried vials. The content of each vial dosed at 50 mcg of bFGF or CM-FGF is dissolved in 1.0 ml of HPLC grade water, then a pool is made with all prepared solutions.

Chromatographic (HPLC) conditions:

The standard and sample solution are alternatively injected at least 3 times into the liquid chromatograph under the following experimental conditions:

| Column temperature | room temperature (22 ± 2° C) | | |
|---|---|---|---|
| Mobile phase flow-rate | 1 ml/min | | |
| Analytical wavelength | 210 ± 1 nm | | |
| Gradient conditions | time (min) | A% | B% |
| | 0 | 75 | 25 |
| | 20 | 60 | 40 |
| | 25 | 60 | 40 |
| | 30 | 75 | 25 |
| Detector sensitivity | the detector "computer" output is connected to integrator for maximum sensitivity | | |
| Injection volume | 100 mcl | | |
| Integrating recorder attenuation | 256 | | |
| Chart speed | 0.5 cm/min | | |

EXAMPLE 2 a) Formulation of bFGF composition stabilised with sodium carboxymethylcellulose

| | Per vial* | per 2,000 vials* |
|---|---|---|
| FCE 26184* | 0.0604 mg* | 120.8 mg* |
| Sodium carboxymethyl-cellulose | 1.0500 mg | 2.1 g |
| 1,4-dithiothreitol | 0.1050 mg | 210.0 mg |
| Mannitol | 21.0000 mg | 42.0 g |
| 0.01N NaOH or 0.01N HCl q.s. to | pH = 6 | pH = 6 |
| Water for Injections** q.s. to | 1.05 ml | 2.1 l |

*including 15% overage to compensate for losses during manufacture
**during freeze-drying water for injections is removed
***a 5% overfill of the bFGF sodium carboxymethyl-cellulose/DTT/mannitol solution is included b) Formulation of bFGF composition stabilized with Polysorbated 80 and cysteine

| | Per vial* | per 2,000 vials* |
|---|---|---|
| FCE 26184* | 0.0604 mg* | 120.8 mg* |
| Cysteine | 0.0105 mg | 21.0 mg |
| 1,4-dithiothreitol | 0.1050 mg | 210.0 mg |
| Mannitol | 21.0000 mg | 42.0 g |
| Polysorbate 80 | 0.0525 mg | 105.0 mg |
| 0.01N NaOH or 0.01N HCl q.s. to | pH = 6 | pH = 6 |
| Water for Injections** q.s. to | 1.05 ml | 2.1 l |

*including 15% overage to compensate for losses during manufacture
**during freeze-drying water for injections is removed
***a 5% overfill of the bFGF sodium carboxymethyl-cellulose/DTT/mannitol solution is included Both formulations were freeze dried and individual vials are sealed under nitrogen.

c) Formulation of CM-FGF composition stabilised with sodium carboxymethylcellulose

| | Per vial*** | per 2,000 vials*** |
|---|---|---|
| CM-FGF* | 0.05 mg* | 100 mg |
| Sodium carboxymethyl-cellulose | 1.00 mg | 2.0 g |
| 1,4-dithiothreitol | 0.10 mg | 200.0 mg |
| Mannitol | 20.00 mg | 40.0 g |
| 0.01N NaOH or 0.01N HCl q.s. to | pH = 6 | pH = 6 |
| Water for Injections** q.s. to | 1.05 ml | 2.1 l |

*including 15% overage to compensate for losses during manufacture
**during freeze-drying water for injections is removed
***a 5% overfill of the bFGF sodium carboxymethyl-cellulose/DTT/mannitol solution is included d) Formulation of CM-FGF composition stabilized with Polysorbated 80 and cysteine

| | Per vial* | per 2,000 vials* |
|---|---|---|
| CM-FGF* | 0.05 mg* | 100.0 mg* |
| Cysteine | 0.01 mg | 20 mg |
| Mannitol | 20 mg | 40.0 g |
| Polysorbate 80 | 0.05 mg | 100.0 mg |
| 0.01N NaOH or 0.01N HCl q.s. to | pH = 6 | pH = 6 |
| Water for Injections** q.s. to | 1.05 ml | 2.1 l |

*including 15% overage to compensate for losses during manufacture
**during freeze-drying water for injections is removed
***a 5% overfill of the bFGF sodium carboxymethyl-cellulose/DTT/mannitol solution is included Both formulations were freeze-dried and individual vials are sealed under nitrogen.

e) Formulation of CM-FGF composition stabilized with Polysorbated 80 and cysteine

| | Per vial*** | per 2,000 vials*** |
|---|---|---|
| CM-FGF | 0.05 mg* | 100 mg* |
| Cysteine | 0.01 mg | 20 mg |
| 1,4-Dithiothreitol | 0.10 mg | 200 mg |
| Mannitol | 20 mg | 40.0 g |
| Polysorbate 80 | 0.05 mg | 100.0 mg |

-continued

|  | Per vial*** | per 2,000 vials*** |
|---|---|---|
| 0.01N NaOH or 0.01 N HCl q.s. to | pH = 6 | pH = 6 |
| Water for Injections** q.s. to | 1.05 ml | 2.1 l |

*including 15% overage to compensate for losses during manufacture
**during freeze-drying water for injections is removed
***a 5% overfill of the bFGF sodium carboxymethyl-cellulose/DTT/mannitol solution is included Both formulations were freeze dried and individual vials are sealed under nitrogen.

EXAMPLE 3

Stability of Compositions of the Invention

Freeze dried vials containing compositions according to the present invention comprising abut 50 μg of bFGF were examined for long term stability over various periods of time at different temperatures. The results are shown in Tables 3 to 22. The following parameters were examined and the acceptable standards are also given.

| | |
|---|---|
| Appearance | colourless glass vials containing a compact, white freeze-dried cake or mass, determined by visual inspection. |
| Identification | * same molecular weight band as a working standard of FCE 26184 or CM-FGF, under both reducing and denaturing conditions, by electrophoresis (SDS PAGE) using the Phast System (Registered Trade Mark), available from Pharmacia LKB Biotechnology, Uppsala, Sweden. |
| RP-HPLC assay | 90-110% of the labelled amount |
| Bioassay (stimulation of DNA synthesis in 3T3 cells) | R = 1.0 ± 0.35, when the values expressed as titre of the formulation, calculated by a parallel line assay measured on $^3$H-TdR incorporation in BALB/3T3 cells, using a FICE internal standard of FCE 26184. |
| Sterility | sterile |
| Water | not more than 3% |
| Appearance after reconstitution * | clear and clean colourless solution, free from visible particles of foreign matter |
| pH after reconstitution * | 5.0–7.0 |

* The vials are dissolved in 5 ml of the required solvent

TABLE 3

Accelerated stability data of FCE 26184 freeze-dried vials - Batch P8199/10/C
Active drug substance Batch No OP49
Composition of Example 2(a)

| | Initial | 25° C. | | |
|---|---|---|---|---|
| Tests | control | 1 week | 2 weeks | 4 weeks |
| Appearance | Complies | | Unchanged | |
| SDS PAGE | A | A | A | A |
| RP-HPLC assay | | | | |
| mcg/vial | 49.88 | 50.93 | 49.63 | 52.07 |
| % initial | 100.0 | 102.1 | 99.5 | 104.4 |
| Bioassay | n.d. | n.d. | n.d. | n.d. |

TABLE 3-continued

Accelerated stability data of FCE 26184 freeze-dried vials - Batch P8199/10/C
Active drug substance Batch No OP49
Composition of Example 2(a)

| | Initial | 25° C. | | |
|---|---|---|---|---|
| Tests | control | 1 week | 2 weeks | 4 weeks |
| Water % | 0.9 | 1.2 | 1.0 | 1.0 |
| Appearance (reconstituted solution) | Complies | | Unchanged | |
| pH (reconstituted solution) | 6.0 | 6.0 | 6.1 | 6.0 |

A = intense band at the correct MW
n.d. = not determined

TABLE 4

Accelerated stability data of FCE 26184 freeze-dried vials - Batch P8199/10/C
Active drug substance Batch No OP49
Composition of Example 2(a)

| | Initial | 35° C. | | |
|---|---|---|---|---|
| Tests | control | 1 week | 2 weeks | 4 weeks |
| Appearance | Complies | | Unchanged | |
| SDS PAGE | A | A | A | A |
| RP-HPLC assay | | | | |
| mcg/vial | 49.88 | 50.83 | 46.84 | 48.73 |
| % initial | 100.0 | 101.9 | 93.9 | 97.7 |
| Bioassay | n.d. | n.d. | n.d. | n.d. |
| Water % | 0.9 | 0.8 | 0.9 | 0.9 |
| Appearance (reconstituted solution) | Complies | | Unchanged | |
| pH (reconstituted solution) | 6.0 | 5.9 | 6.0 | 6.0 |

A = intense band at the correct MW
n.d. = not determined

TABLE 5

Long term stability data of FCE 26184 freeze-dried vials - Batch TF/23600 Active drug substance Batch No. OP51/A
Composition of Example 2 (a)

| | Initial | 2°C. | | | | |
|---|---|---|---|---|---|---|
| Tests | Control | 2 mos | 3 mos | 6 mos | 9 mos | 12 mos |
| Appearance | Complies | | | Unchanged | | |
| SDS PAGE | A | n.d. | A | n.d. | A | A |
| RP-HPLC assay | | | | | | |
| mg/vial | 49.69 | 49.94 | 52.17 | 50.02 | 47.30 | 48.58 |
| % initial | 100.00 | 100.5 | 105.0 | 100.7 | 95.1 | 97.8 |
| Bioassay | Within the limits | n.d. | n.d. | n.d. | Within the limits | Within the limits |
| Water % | 1.5 | 1.8 | 1.5 | 1.9 | 1.7 | n.d. |

TABLE 5-continued

Long term stability data of FCE 26184 freeze-dried vials - Batch TF/23600 Active drug substance Batch No. OP51/A Composition of Example 2 (a)

| Tests | Initial Control | 2°C. | | | | |
|---|---|---|---|---|---|---|
| | | 2 mos | 3 mos | 6 mos | 9 mos | 12 mos |
| Appearance (reconstituted solution) | Complies | | | Unchanged | | |
| pH (reconstituted solution) | 6.0 | 6.0 | 6.0 | 6.0 | 6.0 | 5.6 |

A = intense band at the correct MW
n.d. = not determined

TABLE 6

Long term stability data of FCE 26184 freeze-dried vials - Batch TF/23600 Active drug substance Batch No. OP51/A Composition of Example 2 (a)

| Tests | Initial Control | 8° C. | | | | | |
|---|---|---|---|---|---|---|---|
| | | 2 mos. | 3 mos. | 4 mos. | 6 mos. | 9 mos. | 12 mos. |
| Appearance | Complies | | | unchanged | | | |
| SDS PAGE | A | n.d. | A | n.d. | n.d. | A | A |
| RP-HPLC assay | | | | | | | |
| mcg/vial | 49.69 | 49.02 | 52.97 | 49.09 | 50.49 | 50.50 | 49.46 |
| % initial | 100.0 | 98.6 | 106.6 | 98.8 | 101.6 | 101.6 | 99.5 |
| Bioassay | Within the limits | Within the limits | n.d. | n.d. | n.d. | n.d. | n.d. |
| Water % | 1.5 | 1.0 | 1.2 | 1.4 | 1.6 | 1.6 | n.d. |
| Appearance (reconstituted) solution) | Complies | | | unchanged | | | |
| pH (reconstituted solution) | 6.0 | 6.0 | 5.9 | n.d. | 6.0 | 5.9 | 5.7 |
| Sterility | sterile | n.d. | n.d. | n.d. | n.d. | n.d. | sterile |

A = intense band at the correct MW
n.d. = not determined

TABLE 7

Long term stability data of FCE 26184 freeze-dried vials - Batch TF/23600 Active drug substance Batch No. OP51/A Composition of Example 2 (a)

| Tests | Initial Control | 15° C. | | | | | |
|---|---|---|---|---|---|---|---|
| | | 2 mos. | 3 mos. | 4 mos. | 6 mos. | 9 mos. | 12 mos. |
| Appearance | Complies | | | Unchanged | | | |
| SDS PAGE | A | n.d. | A | n.d. | n.d. | A | A |
| RP-HPLC assay | | | | | | | |
| mcg/vial | 49.69 | 46.32 | 52.12 | 49.94 | 49.00 | 51.10 | 48.22 |

TABLE 7-continued

Long term stability data of FCE 26184 freeze-dried vials - Batch TF/23600 Active drug substance Batch No. OP51/A Composition of Example 2 (a)

| Tests | Initial Control | 15° C. | | | | | |
|---|---|---|---|---|---|---|---|
| | | 2 mos. | 3 mos. | 4 mos. | 6 mos. | 9 mos. | 12 mos. |
| % initial Bioassay | 100.0 Within the limits | 93.2 n.d. | 104.9 n.d. | 100.5 n.d. | 98.6 n.d. | 103.0 Within the limits | 97.0 n.d. |
| Water % | 1.5 | 2.0 | 1.5 | 1.4 | 1.7 | 1.8 | n.d. |
| Appearance (reconstituted solution) | Complies | | | Unchanged | | | |
| pH (reconstituted solution) | 6.0 | 5.9 | 5.9 | n.d. | 6.0 | 5.9 | 5.7 |

A = intense band at the correct MW
n.d. = not determined

TABLE 8

Long term stability data of FCE 26184 freeze-dried vials - Batch TF/23600 Active drug substance Batch No. OP51/A Composition of Example 2 (a)

| Tests | Initial Control | 25° C. | | | | | | |
|---|---|---|---|---|---|---|---|---|
| | | 1 mo. | 2 mos. | 3 mos. | 4 mos. | 6 mos. | 9 mos. | 12 mos. |
| Appearance | Complies | | | Unchanged | | | | |
| SDS PAGE | A | A | n.d. | B | n.d. | n.d. | B | B |
| RP-HPLC assay | | | | | | | | |
| mcg/vial | 49.69 | 49.35 | 48.33 | 46.21 | 45.22 | 43.70 | n.d. | 46.42 |
| % initial | 100.0 | 99.3 | 97.3 | 93.0 | 91.0 | 87.9 | n.d. | 93.4 |
| Bioassay | Within the limits | n.d. | Within the limits | n.d. | n.d. | n.d. | n.d. | Within the limits |
| Water % | 1.5 | 1.5 | 1.8 | 1.7 | 1.8 | 1.8 | 1.7 | n.d. |
| Appearance (reconstituted solution) | Complies | | | | Unchanged | | | |
| pH (reconstituted solution) | 6.0 | 5.8 | 5.7 | 5.9 | 6.0 | 6.0 | 5.8 | 5.7 |

A = intense band at the correct MW
B = presence of secondary bands, both at higher MW
n.d. = not determined.

TABLE 9

Accelerated stability data of FCE 26184 freeze-dried vials - Batch TF/23600 Active drug substance Batch No. OP51/A Composition of Example 2 (a)

| Tests | Initial control | 35°C. | | | | | | |
|---|---|---|---|---|---|---|---|---|
| | | 8 days | 15 days | 1 mo. | 2 mos. | 3 mos. | 4 mos. | |
| Appearance | Complies | | | Unchanged | | | | |
| SDS PAGE | A | n.d. | n.d. | B | n.d. | B | n.d. | |
| RP-HPLC assay | | | | | | | | |
| mcg/vial | 49.69 | 48.80 | 47.80 | 42.30 | 44.39 | 41.04 | 42.24 | |
| % initial | 100.00 | 98.2 | 96.2 | 85.1 | 89.3 | 82.6 | 85.0 | |
| Bioassay | Within the limits | n.d. | n.d. | Within the limits | n.d. | n.d. | n.d. | |
| Water % | 1.5 | 1.5 | 1.1 | 1.6 | 1.2 | 1.5 | 1.3 | |
| Appearance (reconstituted solution) | Complies | | | Unchanged | | | | |
| pH (reconstituted solution) | 6.0 | 5.9 | 5.8 | 5.8 | 5.8 | 6.0 | 6.1 | |

TABLE 9-continued

Accelerated stability data of FCE 26184 freeze-dried vials - Batch TF/23600 Active drug substance Batch No. OP51/A Composition of Example 2 (a)

| Tests | Initial control | 35°C. | | | | | |
|---|---|---|---|---|---|---|---|
| | | 8 days | 15 days | 1 mo. | 2 mos. | 3 mos. | 4 mos. |
| solution) | | | | | | | |

A = intense band at the correct MW
B = presence of secondary bands at higher MW
n.d. = not determined

TABLE 10

Accelerated stability data of FCE 26184 freeze-dried vials - Batch TF/23600 Active drug substance Batch No. OP51/A Composition of Example 2(a)

| Tests | Initial control | LCT + 100 F.C. | | |
|---|---|---|---|---|
| | | 8 days | 15 days | 1 mo. |
| Appearance | Complies | | Unchanged | |
| SDS PAGE | A | n.d. | n.d. | A |
| RP-HPLC assay | | | | |
| mcg/vial | 49.69 | 49.20 | 51.65 | 48.50 |
| % initial | 100.0 | 99.0 | 103.9 | 97.6 |
| Bioassay | Within the limits | n.d. | n.d. | n.d. |
| Water % | 1.5 | 1.4 | 1.0 | 1.0 |
| Appearance (reconstituted solution) | Complies | | Unchanged | |
| pH (reconstituted solution) | 6.0 | 6.0 | 5.9 | 5.9 |

LCT = Light Cabinet Temperature (28° ± 2° C.)
F.C. = Foot Candles
A = intense band at the correct MW
n.d. = not determined

TABLE 11

Long term stability data of FCE 26184 freeze-dried vials - Batch TF/23625 Active drug substance Batch No. OP48 Composition of Example 2(a)

| Tests | Initial control | 2° C. | | |
|---|---|---|---|---|
| | | 2 mos. | 6 mos. | 9 mos. |
| Appearance | Complies | | Unchanged | |
| SDS PAGE | A | A | A | A |
| RP-HPLC assay | | | | |
| mcg/vial | 49.43 | 49.38 | 50.18 | 47.18 |
| % initial | 100.0 | 99.9 | 101.5 | 95.4 |
| Bioassay | Within the limits | n.d. | n.d. | Within the limits |
| Water % | 1.0 | 1.2 | 1.4 | 1.5 |
| Appearance (reconstituted solution) | Complies | | Unchanged | |
| pH (reconstituted solution) | 5.4 | 5.4 | 4.7 | 4.7 |

A = intense band at the correct MW
n.d. = not determined

TABLE 12

Long term stability data of FCE 26184 freeze-dried vials - Batch TF/23625 Active drug substance Batch No. OP48 Composition of Example 2(a)

| Tests | Initial control | 8° C. | | | |
|---|---|---|---|---|---|
| | | 2 mos. | 3 mos. | 6 mos. | 9 mos. |
| Appearance | Complies | | Unchanged | | |
| SDS PAGE | A | A | n.d. | n.d. | A |
| RP-HPLC assay | | | | | |
| mcg/vial | 49.43 | 48.34 | 52.10 | n.d. | 45.46 |
| % initial | 100.0 | 97.8 | 105.4 | n.d. | 92.0 |
| Bioassay | Within the limits | n.d. | n.d. | n.d. | n.d. |
| Water % | 1.0 | 1.2 | 1.1 | 1.3 | 1.1 |
| Appearance (reconstituted solution) | Complies | | Unchanged | | |
| pH (reconstituted solution) | 5.4 | 5.4 | 5.4 | 5.6 | 5.5 |
| Sterility | sterile | n.d. | n.d. | n.d. | n.d. |

A = intense band at the correct MW
n.d. = not determined

TABLE 13

Long term stability data of FCE 26184 freeze-dried vials - Batch TF/23625 Active drug substance Batch No. OP48 Composition of Example 2(a)

| Tests | Initial control | 15° C. | | | |
|---|---|---|---|---|---|
| | | 2 mos. | 3 mos. | 6 mos. | 9 mos. |
| Appearance | Complies | | Unchanged | | |
| SDS PAGE | A | A | A | n.d. | A |
| RP-HPLC assay | | | | | |
| mcg/vial | 49.43 | 49.03 | 49.8 | 52.25 | 46.32 |
| % initial | 100.0 | 99.2 | 100.7 | 105.7 | 93.7 |
| Bioassay | Within the limits | n.d. | n.d. | n.d. | n.d. |
| Water % | 1.0 | 1.1 | 1.2 | 1.2 | 1.4 |
| Appearance (reconstituted solution) | Complies | | Unchanged | | |
| pH (reconstituted solution) | 5.4 | 5.4 | 5.4 | 5.6 | 5.4 |

A = intense band at the correct MW
n.d. = not determined

TABLE 14

Long term stability data of FCE 26184 freeze-dried vials - Batch TF/23625 Active drug substance Batch No. OP48 Composition of Example 2(a)

| Tests | Initial control | 25° C. | | | | |
|---|---|---|---|---|---|---|
| | | 1 mo. | 2 mos. | 3 mos. | 6 mos. | 9 mos. |
| Appearance | Complies | | Unchanged | | | |
| SDS PAGE | A | A | A | A | n.d. | B |
| RP-HPLC assay | | | | | | |
| mcg/vial | 49.43 | 46.61 | 47.06 | 51.2 | 48.82 | 45.01 |
| % initial | 100.0 | 94.3 | 95.2 | 103.6 | 98.8 | 91.1 |
| Bioassay | Within the | n.d. | n.d. | n.d. | n.d. | Within the |

TABLE 14-continued

Long term stability data of FCE 26184 freeze-dried vials -
Batch TF/23625 Active drug substance Batch No. OP48
Composition of Example 2(a)

| | Initial | 25° C. | | | | |
|---|---|---|---|---|---|---|
| Tests | control | 1 mo. | 2 mos. | 3 mos. | 6 mos. | 9 mos. |
| Water % | limits 1.0 | 1.2 | 1.1 | 1.1 | 1.2 | limits 1.2 |
| Appearance (reconstituted solution) | Complies | | Unchanged | | | |
| pH (reconstituted solution) | 5.4 | 5.6 | 5.4 | 5.4 | 5.7 | 5.5 |

A = intense band at the correct MW
n.d. = not determined

TABLE 15

Long term stability data of FCE 26184 freeze-dried vials -
Batch TF/23625 Active drug substance Batch No. OP48
Composition of Example 2(a)

| | Initial | 30°C. | | | | |
|---|---|---|---|---|---|---|
| Tests | control | 1 mo. | 2 mos. | 3 mos. | 6 mos. | 9 mos. |
| Appearance | Complies | | | Unchanged | | |
| SDS PAGE | A | A | A | A | n.d. | n.d. |
| RP-HPLC assay | | | | | | |
| mcg/vial | 49.43 | 45.82 | 49.18 | 51.5 | 48.48 | n.d. |
| % Initial | 100.0 | 92.7 | 99.5 | 104.2 | 98.1 | n.d. |
| Bioassay | Within the limits | n.d. | n.d. | n.d. | n.d. | n.d. |
| Water % | 1.0 | 1.2 | 1.1 | 1.3 | 1.3 | n.d. |
| Appearance (reconstituted solution) | Complies | | | Unchanged | | |
| pH (reconstituted solution) | 5.4 | 5.5 | 5.5 | 5.4 | 5.7 | n.d. |

A = intense band at the correct MW
n.d. = not determined

TABLE 16

Accelerated stability data of FCE 26184 freeze-dried
vials - Batch TF/23625 Active drug substance Batch No. OP48
Composition of Example 2(a)

| | Initial | 35° C. | | |
|---|---|---|---|---|
| Tests | control | 15 days | 1 mo. | 2 mos. |
| Appearance | Complies | | Unchanged | |
| SDS PAGE | A | A | A | A |
| RP-HPLC assay | | | | |
| mcg/vial | 49.43 | n.d. | 45.18 | 48.14 |
| % initial | 100.0 | | 91.4 | 97.4 |
| Bioassay | Within the limits | n.d. | n.d. | n.d. |
| Water % | 1.0 | 1.5 | 1.4 | 1.2 |

TABLE 16-continued

Accelerated stability data of FCE 26184 freeze-dried
vials - Batch TF/23625 Active drug substance Batch No. OP48
Composition of Example 2(a)

| | Initial | 35° C. | | |
|---|---|---|---|---|
| Tests | control | 15 days | 1 mo. | 2 mos. |
| Appearance (reconstituted solution) | Complies | | Unchanged | |
| pH (reconstituted solution) | 5.4 | 5.5 | 5.5 | 5.5 |

A = intensae band at the correct MW
n.d. = not determined

TABLE 17

Long term stability data of FCE 26184 freeze-
dried vials - batch P8199/10/I Active drug substance
Batch No. OP49
Composition of Example 2(b)

| | Initial | 25° C. | | |
|---|---|---|---|---|
| Tests | control | 1 week | 2 weeks | 4 weeks |
| Appearance | Complies | | Unchanged | |
| SDS PAGE | A | A | A | A |
| RP-HPLC assay | | | | |
| mcg/vial | 51.08 | 53.58 | n.d. | 46.43 |
| % initial | 100.0 | 104.9 | | 90.9 |
| Bioassay | n.d. | n.d. | n.d. | n.d. |
| Water % | 0.8 | 0.9 | 0.9 | 1.0 |
| Appearance (reconstituted solution) | Complies | | Unchanged | |
| pH (reconstituted solution) | 6.0 | 6.2 | 6.1 | 6.2 |

A = intense band at the correct MW
n.d. = not determined

TABLE 18

Accelerated stability data of FCE 26184 freeze-dried
vials - Batch P8199/10/I Active drug substance
Batch No. OP49
Composition of Example 2(b)

| | Initial | 35° C. | | |
|---|---|---|---|---|
| Tests | control | 1 week | 2 weeks | 4 weeks |
| Appearance | Complies | | Unchanged | |
| SDS PAGE | A | A | A | A |
| RP-HPLC assay | | | | |
| mcg/vial | 51.08 | 57.36 | 57.67 | 43.62 |
| % initial | 100.0 | 112.3 | 112.9 | 85.4 |
| Bioassay | n.d. | n.d. | n.d. | n.d. |
| Water % | 0.8 | 0.8 | 0.8 | 0.9 |
| Appearance (reconstituted solution) | Complies | | Unchanged | |
| pH (reconstituted solution) | 6.0 | 6.3 | 6.3 | 6.3 |

A = intense band at the correct MW
n.d. = not determined

TABLE 19

Long term stability data of FCE 26184 freeze-dried vials - Batch TF/23607 Active drug substance Batch No. OP51/A
Composition of Example 2(b)

| Tests | Initial control | 2° C. 2 mos. | 2° C. 3 mos. |
|---|---|---|---|
| Appearance | Complies | Unchanged | |
| SDS PAGE | A | A | A |
| RP-HPLC assay | | | |
| mcg/vial | 52.13 | 50.93 | 51.56 |
| % initial | 100.0 | 97.7 | 98.9 |
| Bioassay | Within the limits | n.d. | n.d. |
| Water % | 0.8 | 1.0 | 1.2 |
| Appearance (reconstituted solution) | Complies | Unchanged | |
| pH (reconstituted solution) | 6.1 | 6.4 | 6.3 |

A=intense band at the correct MW
n.d.=not determined

TABLE 20

Long term stability data of FCE 26184 freeze-dried vials - Batch TF/23607 Active drug substance Batch No. OP51/A
Composition of Example 2(b)

| Tests | Initial control | 25° C. 1 mo. | 25° C. 2 mos. | 25° C. 3 mos. | 25° C. 4 mos. |
|---|---|---|---|---|---|
| Appearance | Complies | Unchanged | | | |
| SDS PAGE | A | A | A | A | A |
| RP-HPLC assay | | | | | |
| mcg/vial | 52.13 | 49.45 | 42.63 | 43.48 | 46.50 |
| % initial | 100.0 | 94.9 | 81.8 | 83.4 | 89.1 |
| Bioassay | Within the limits | n.d. | Within the limits | n.d. | n.d. |
| Water % | 0.8 | 0.8 | 0.9 | 1.0 | 1.1 |
| Appearance (reconstituted solution) | Complies | Unchanged | | | |
| pH (reconstituted solution) | 6.1 | 6.3 | 6.2 | 6.1 | 6.3 |

A=intense band at the correct MW
n.d.=not determined

TABLE 21

Accelerated stability data of FCE 26184 freeze-dried vials - Batch TF/23607 Active drug substance Batch No. OP51/A
Composition of Example 2(b)

| Tests | Initial control | 35° C. 8 days | 35° C. 15 days | 35° C. 1 mo. | 35° C. 2 mos. | 35° C. 3 mos. |
|---|---|---|---|---|---|---|
| Appearance | Complies | Unchanged | | | | |
| SDS PAGE | A | A | A | A | A | A |
| RP-HPLC assay | | | | | | |
| mcg/vial | 52.13 | 52.15 | 47.85 | 41.95 | 36.90 | 34.87 |
| % initial | 100.0 | 100.0 | 91.8 | 80.5 | 70.8 | 66.9 |
| Bioassay | Within the limits | n.d. | n.d. | Within the limits | n.d. | n.d. |
| Water % | 0.8 | 1.0 | 1.0 | 0.9 | 1.2 | 1.5 |
| Appearance (reconstituted solution) | Complies | Unchanged | | | | |
| pH (reconstituted solution) | 6.1 | 6.3 | 6.3 | 6.3 | 6.3 | 6.1 |

A = intense band at the correct MW
n.d. = not determined

TABLE 22

Accelerated stability data of freeze-dried vials - Batch P4 Active drug substance Batch No. 910116-CM
Composition of Example 2(c)

| Tests | Initial control | 15 days 35° C. | 15 days 45° C. | 1 month 4° C. | 1 month 25° C. | 1 month 35° C. |
|---|---|---|---|---|---|---|
| RP-HPLC assay | | | | | | |
| mcg/vial | 53.54 | n.d. | 52.61 | 56.21 | 54.24 | 56.65 |
| % initial | 100.0 | | 98.2 | 105.0 | 101.3 | 105.8 | n.d.=not determined
Similar stability could be observed for the composition of Examples 2(d) and 2(e).

We claim:

1. A lyophilized composition comprising a pharmaceutically acceptable bulking agent, a fibroblast growth factor (FGF) in an amount from 0.01 to 5% of the weight of the bulking agent and an alkali metal salt of a carboxyalkyl cellulose in an amount of from 2.5 to 10% by weight of the bulking agent, wherein said alkali metal salt is a sodium or potassium salt of a carboxy $C_1$–$C_4$ alkyl cellulose.

2. A composition according to claim 1 in which the alkali metal salt is sodium carboxymethyl cellulose.

3. A lyophilized composition comprising a fibroblast growth factor (FGF), a pharmaceutical acceptable bulking agent and an amount of a mixture of a polyoxyethylene sorbitan fatty acid ester and cysteine effective to stabilize said FGF, wherein said ester is selected from the group consisting of polysorbates 20, 40, 60, 65, 80 and 85.

4. A composition according to claim 3 in which the polyoxyethylene fatty acid ester is polysorbate 80.

5. A composition according to claim 1 or 3 which additionally comprises an antioxidant.

6. A composition according to claim 5 in which the antioxidant is dithiothreitol.

7. A composition according to claim 1 or 3 in which the bulking agent is mannitol, lactose, polyvinylpyrrolidone, galactitol or trehalose.

8. A composition according to claim 1 or 3 in a sealed sterile glass vial.

9. A composition according to claim 1 or 3 wherein the fibroblast growth factor is basic FGF.

10. A composition according to claim 1 or 3 wherein the fibroblast growth factor is a basic FGF having the amino acid sequence from position 10 to position 155 shown in SEQ ID NO:1 in which the Cys residues at positions 78 and 96 in SEQ ID NO:1 are carboxymethylated.

11. A method of preparing the lyophilized composition of claim 1 comprising mixing said fibroblast growth factor, said pharmaceutically acceptable bulking agent and said alkali metal salt in water to prepare an aqueous solution, and lyophilizing said aqueous solution.

12. A method according to claim 11, in which the alkali metal salt is sodium carboxymethyl cellulose.

13. A method of preparing the lyophilized composition of claim 3, comprising mixing said FGF, said pharmaceutically acceptable bulking agent, said polyoxyethylene sorbitan fatty acid ester and said cysteine in water to prepare an aqueous solution, and lyophilizing said aqueous solution.

14. A method according to claim 11 or 13, in which the bulking agent is mannitol, lactose, polyvinylpyrrolidone, galactitol or trehalose.

15. A kit comprising (i) the lyophilized composition of claim 1 and (ii) a sterile solution for reconstituting said composition.

16. A kit according to claim 15 in which the alkali metal salt is sodium carboxmethyl cellulose.

17. A kit comprising (i) the lyophilized composition of claim 3 and (ii) a sterile solution for reconstituting said composition.

18. A kit according to claim 15 or 17 in which the lyophilized composition additionally comprises an antioxidant.

19. A kit according to claim 15 or 17, in which the bulking agent is mannitol, lactose, polyvinylpyrrolidone, galactitol or trehalose.

20. A method for preparing an aqueous fibroblast growth factor (FGF) solution comprising reconstituting the lyophilized composition of claim 1 with a sterile aqueous diluent.

21. A method according to claim 20 in which the alkali metal salt is sodium carboxymethyl cellulose.

22. A method for preparing an aqueous fibroblast growth factor (FGF) solution comprising reconstituting the lyophilized composition of claim 3 with a sterile aqueous diluent.

23. A method according to claim 20 or 22 in which the lyophilized composition additionally comprises an antioxidant.

24. A method according to claim 20 or 22 in which the bulking agent is mannitol, lactose, polyvinylpyrrolidone, galactitol or trehalose.

25. A lyophilized composition, comprising:

a fibroblast growth factor (FGF), a pharmaceutically acceptable bulking agent and an amount of a mixture of a polysorbate 80 and cysteine effective to stabilize said FGF.

26. A method of preparing a lyophilized composition comprising a fibroblast growth factor (FGF), a pharmaceutically acceptable bulking agent and an amount of a mixture of polysorbate 80 and cysteine effective to stabilize said FGF, comprising:

mixing said FGF, said pharmaceutically acceptable bulking agent, said polysorbate 80 and cysteine in water to prepare an aqueous solution, and lyophilizing said aqueous solution.

27. A kit comprising:

(i) a lyophilized composition comprising a fibroblast growth factor (FGF), a pharmaceutically acceptable bulking agent and an amount of a mixture of polysorbate 80 and cysteine effective to stabilize said FGF, and (ii) a sterile solution for reconstituting said composition.

28. A method of stabilizing a lyophilized composition comprising a pharmaceutically acceptable bulking agent and a fibroblast growth factor (FGF) in an amount from 0.01 to 5% of the weight of the bulking agent, which method comprises incorporating a sodium or potassium salt of a carboxy $C_1$–$C_4$ alkyl cellulose into said composition in an amount of from 2.5 to 10% by weight of the bulking agent.

29. A method according to claim 28, wherein said salt is incorporated by (i) preparing a solution containing the bulking agent, the FGF and the salt; and (ii) lyophilizing the solution.

30. A method according to claim 28 or 29 in which an antioxidant is additionally incorporated into the composition.

31. A method according to claim 28 or 29 in which the bulking agent is selected from the group consisting of mannitol, lactose, polyvinylpyrrolidone, galactitol and trehalose.

32. A method according to claim 28 or 29 in which the salt is sodium carboxymethyl cellulose.

* * * * *